US 8,764,818 B2

(12) United States Patent
Gregg

(10) Patent No.: US 8,764,818 B2
(45) Date of Patent: Jul. 1, 2014

(54) HEART VALVE REPLACEMENT

(75) Inventor: Peter W. Gregg, Santa Cruz, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 13/553,217

(22) Filed: Jul. 19, 2012

(65) Prior Publication Data

US 2013/0066419 A1    Mar. 14, 2013

Related U.S. Application Data

(60) Provisional application No. 61/509,807, filed on Jul. 20, 2011.

(51) Int. Cl.
*A61F 2/24* (2006.01)

(52) U.S. Cl.
USPC .......... 623/2.1; 623/1.26; 623/2.17; 623/2.18

(58) Field of Classification Search
CPC .............................. A61F 2/2412; A61F 2/2418
USPC ................. 623/1.24, 1.26, 2.1–2.19
See application file for complete search history.

(56) References Cited

U.S. PATENT DOCUMENTS

| | | | |
|---|---|---|---|
| 4,172,295 A | 10/1979 | Batten | |
| 4,218,782 A | 8/1980 | Rygg | |
| 4,687,483 A | 8/1987 | Fisher et al. | |
| 5,549,666 A | 8/1996 | Hata et al. | |
| 5,562,729 A | 10/1996 | Purdy et al. | |
| 5,843,161 A | 12/1998 | Solovay | |
| 5,861,028 A | 1/1999 | Angell | |
| 5,961,549 A | 10/1999 | Nguyen et al. | |
| 6,102,944 A | 8/2000 | Huynh et al. | |
| 6,245,105 B1 | 6/2001 | Nguyen et al. | |
| 6,254,636 B1 | 7/2001 | Peredo | |
| 6,283,994 B1 | 9/2001 | Moe et al. | |
| 6,334,873 B1 | 1/2002 | Lane et al. | |
| 6,378,221 B1 | 4/2002 | Ekholm, Jr. et al. | |
| 6,413,275 B1 | 7/2002 | Nguyen et al. | |
| 6,458,153 B1 | 10/2002 | Bailey et al. | |
| 6,553,681 B2 | 4/2003 | Ekholm, Jr. et al. | |
| 6,562,069 B2 | 5/2003 | Cai et al. | |

(Continued)

FOREIGN PATENT DOCUMENTS

WO    01/54624    8/2001
WO    01/54625    8/2001

(Continued)

OTHER PUBLICATIONS

Bartek et al., "Frame-mounted tissue heart valves: technique of construction," Thorax, vol. 29, pp. 51-55, (1975).

(Continued)

*Primary Examiner* — Jason-Dennis Stewart
(74) *Attorney, Agent, or Firm* — Fish & Richardson P.C.

(57) ABSTRACT

A prosthetic heart valve includes a radially expandable stent and a plurality of leaflets. Each leaflet includes a coaptation portion, an arcuate edge, and a belly. The coaptation portion is movable relative to respective coaptation portions of the other leaflets. The arcuate edge has a first end and a second end and is coupled to the stent. The belly extends from the arcuate edge to an axis defined by the first and second ends of the arcuate edge, wherein the ratio of the surface area of the belly to the outer cross-sectional area of the expanded stent is about 0.09 to about 0.16.

20 Claims, 9 Drawing Sheets

(56) References Cited

U.S. PATENT DOCUMENTS

| | | |
|---|---|---|
| 6,575,971 B2 | 6/2003 | Hauck et al. |
| 6,613,086 B1 | 9/2003 | Moe et al. |
| 6,666,885 B2 | 12/2003 | Moe |
| 6,682,559 B2 | 1/2004 | Myers et al. |
| 6,702,845 B1 | 3/2004 | Cully et al. |
| 6,719,789 B2 | 4/2004 | Cox |
| 6,723,123 B1 | 4/2004 | Kazatchkov et al. |
| 6,726,715 B2 | 4/2004 | Sutherland |
| 6,767,362 B2 | 7/2004 | Schreck |
| 6,797,002 B2 | 9/2004 | Spence et al. |
| 6,830,585 B1 | 12/2004 | Artof et al. |
| 6,837,902 B2 | 1/2005 | Nguyen et al. |
| 7,037,333 B2 | 5/2006 | Myers et al. |
| 7,166,126 B2 | 1/2007 | Spence et al. |
| 7,527,647 B2 | 5/2009 | Spence |
| 7,601,117 B2 | 10/2009 | Kute et al. |
| 7,666,504 B2 | 2/2010 | Ochi et al. |
| 7,704,222 B2 | 4/2010 | Wilk et al. |
| 7,736,327 B2 | 6/2010 | Wilk et al. |
| 7,780,726 B2 | 8/2010 | Sequin |
| 7,988,900 B2 | 8/2011 | Beith |
| RE42,818 E | 10/2011 | Cali et al. |
| RE42,857 E | 10/2011 | Cali et al. |
| 8,043,450 B2 | 10/2011 | Cali et al. |
| 8,057,538 B2 | 11/2011 | Bergin et al. |
| 8,075,611 B2 | 12/2011 | Millwee et al. |
| 8,083,908 B2 | 12/2011 | Marton et al. |
| 2003/0229394 A1 | 12/2003 | Ogle et al. |
| 2005/0137688 A1 | 6/2005 | Salahieh et al. |
| 2005/0137689 A1 | 6/2005 | Salahieh et al. |
| 2005/0137692 A1 | 6/2005 | Haug et al. |
| 2005/0137693 A1 | 6/2005 | Haug et al. |
| 2005/0137695 A1 | 6/2005 | Salahieh et al. |
| 2005/0137697 A1 | 6/2005 | Salahieh et al. |
| 2005/0137699 A1 | 6/2005 | Salahieh et al. |
| 2005/0137701 A1 | 6/2005 | Salahieh et al. |
| 2005/0143809 A1 | 6/2005 | Salahieh et al. |
| 2005/0283231 A1 | 12/2005 | Haug et al. |
| 2006/0058872 A1 | 3/2006 | Salahieh et al. |
| 2006/0173524 A1 | 8/2006 | Salahieh et al. |
| 2006/0253191 A1 | 11/2006 | Salahieh et al. |
| 2006/0259136 A1 | 11/2006 | Nguyen et al. |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0203503 A1 | 8/2007 | Salahieh et al. |
| 2007/0244552 A1 | 10/2007 | Salahieh et al. |
| 2008/0125859 A1 | 5/2008 | Salahieh et al. |
| 2008/0183279 A1 | 7/2008 | Bailey et al. |
| 2008/0234814 A1 | 9/2008 | Salahieh et al. |
| 2009/0054969 A1 | 2/2009 | Salahieh et al. |
| 2009/0076598 A1 | 3/2009 | Salahieh et al. |
| 2009/0264997 A1 | 10/2009 | Salahieh et al. |
| 2010/0121434 A1 | 5/2010 | Paul et al. |
| 2010/0219092 A1 | 9/2010 | Salahieh et al. |
| 2012/0053681 A1 | 3/2012 | Alkhatib et al. |

FOREIGN PATENT DOCUMENTS

| | | |
|---|---|---|
| WO | 2005/046528 | 5/2005 |
| WO | 2006/050460 | 5/2006 |
| WO | 2009/042196 | 4/2009 |
| WO | 2010/008549 | 1/2010 |
| WO | 2012/027487 | 3/2012 |

OTHER PUBLICATIONS

Butterfield et al., "Leaflet geometry and function in porcine bioprostheses," European Journal of Cardiothoracic Surgery, vol. 5, pp. 27-32, (1991).

Fisher et al., "An improved pericardial bioprosthetic heart valve—Design and laboratory evaluation," European Journal of Cardiothoracic Surgery, vol. 1, pp. 71-79 (1987).

International Search Report and Witten Opinion issued by the European Patent Office on May 27, 2013, in the international application PCT/US2012/047382, filed on Jul. 19, 2012, 13 pages.

Langdon et al., "Biaxial mechanical/structural effects of equibiaxial strain during crosslinking of bovine pericardial xenograft materials," Biomaterials, vol. 20, pp. 137-153, (1999).

Missirlis et al., "Aortic Valve Mechanics—Part I: Material Properties of Natural Porcine Aortic Valves," Journal of Bioengineering, vol. 2, pp. 287-300, (1978).

Sauren et al., "The Mechanical Properties of Porcine Aortic Valve Tissues," Journal of Biomechanics, vol. 16, No. 5, pp. 327-337, (1983).

Simonescu et al., "Mapping of glutaraldehyde-treated bovine pericardium and tissue selection for bioprosthetic heart valves," Journal of Biomedical Materials Research, vol. 27, pp. 697-704 (1993).

Simonescu, "Artificial Heart Valves," Wiley Encyclopedia of Biomedical Engineering, pp. 1-10, (2006).

Thubrikar et al., "Stress Sharing Between the Sinus and Leaflets of Canine Aortic Valve," Annals of Thoracic Surgery, vol. 42, pp. 434-440, Oct. 1986.

Trowbridge et al., "Pericardial Heterograft Valves: An Assessment of Leaflet Stresses and Their Implications for Heart Valve Design," Journal of Bioengineering, vol. 9, pp. 345-355, Oct. 1987.

Zegdi et al., "Is it Reasonable to Treat All Calcified Stenotic Aortic Valves With a Valved Stent?," Journal of the American College of Cardiology, vol. 51, No. 5, p. 579-584, (2008).

Zioupos et al., "Anisotropic elasticity and strength of glutaraldehyde fixed bovine pericardium for use in pericardial bioprosthetic valves," Journal of Biomedical Materials Research, vol. 28, pp. 49-57, (1994).

International Preliminary Report on Patentablility in International Application No. PCT/US2012/047382, mailed Jan. 30, 2014, 9 pages.

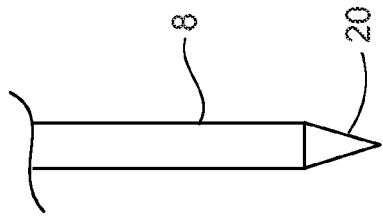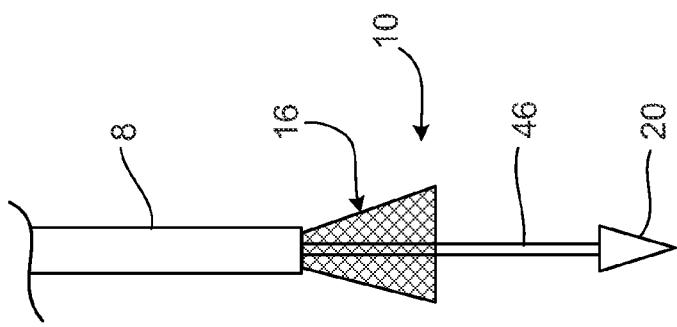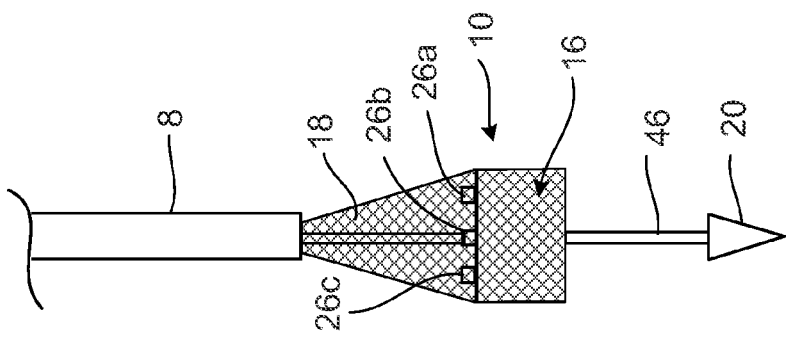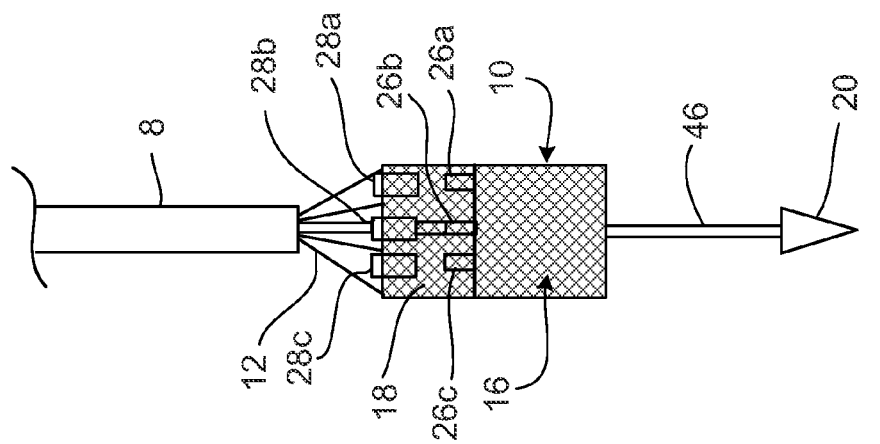

HEART VALVE REPLACEMENT

CROSS-REFERENCE TO RELATED APPLICATION

This application claims priority under 35 USC §119(e) to U.S. Provisional Patent Application Ser. No. 61/509,807, filed on Jul. 20, 2011, the entire contents of which are hereby incorporated by reference.

TECHNICAL FIELD

The following disclosure relates to replacement heart valves and, more particularly, to replacement heart valves including leaflets.

BACKGROUND

Heart valve surgery can be used to repair or replace diseased heart valves. For example, heart valve replacement may be indicated when there is a narrowing of the native heart valve, commonly referred to as stenosis, or when the native valve leaks or regurgitates. Surgery to repair or replace diseased heart valves can be an open-heart procedure, conducted under general anesthesia, in which an incision is made through the patient's sternum (sternotomy), and the patient's heart is stopped while blood flow is rerouted through a heart-lung bypass machine.

Post-surgery, patients temporarily may be confused due to emboli and other factors associated with the heart-lung machine. The first 2-3 days following surgery are spent in an intensive care unit where heart functions can be closely monitored. The average hospital stay is between 1 to 2 weeks, with several more weeks to months required for complete recovery. Given its highly invasive nature, this type of surgery is often unavailable as a treatment option for patients with compromised ability to recover.

SUMMARY

A prosthetic heart valve replaces the function of a native heart valve such that the prosthetic valve regulates the flow of blood through the heart.

In one aspect, a prosthetic heart valve includes a stent and a plurality of leaflets. The stent has an outer cross-sectional area, and the stent is radially expandable to an expanded, unstressed state. Each leaflet includes a coaptation portion movable relative to respective coaptation portions of the other leaflets, an arcuate edge having a first end and a second end, the arcuate edge coupled to the stent, and a belly. The belly extends from the arcuate edge to an axis defined by the first and second ends of the arcuate edge. The ratio of the surface area of the belly to the outer cross-sectional area of the stent in the expanded, unstressed state is about 0.09 to about 0.16.

In some embodiments, the stent in the expanded, unstressed state has an outer diameter of about 20 mm to about 30 mm.

In certain embodiments, the arcuate edge has a radius of about 20 mm to about 50 mm and an included angle of about 35 degrees to about 70 degrees.

In some embodiments, a maximum distance between the arcuate edge and the axis defined by the first and second ends of the arcuate edge is about 2 mm to about 4 mm.

In certain embodiments, the arcuate edges of the respective leaflets are coupled to the stent in a plane. For example, the plane can be defined by an end of the stent.

In some embodiments, the total arc lengths of the arcuate edges of the plurality of leaflets, as coupled to the stent, is about equal to an inner circumference of the expanded stent.

In certain embodiments, each leaflet is substantially symmetrical about an axis of the leaflet extending in a direction from the coaptation portion to the arcuate edge.

In some embodiments, the arcuate edge is opposite the coaptation portion. Each of the plurality of leaflets can further include first and second side portions extending from respective first and second ends of the arcuate edge toward the coaptation portion. Additionally or alternatively, the first and second side portions of each leaflet can be nonparallel to each other. For example, for each leaflet, the maximum width of the coaptation portion can be less than the maximum width of the arcuate edge.

In some embodiments, at least one side portion of each leaflet is sutured to at least one side portion of each of the other leaflets.

In certain embodiments, the included angle between each side portion and a tangent to a respective end of the arcuate edge is greater than about 90 degrees.

In some embodiments, each of the plurality of leaflets has a thickness of between about 0.010 inches to about 0.015 inches.

In certain embodiments, each of the plurality of leaflets is biological tissue. For example, the biological material is one or more of the following: bovine pericardium, equine pericardium, and porcine pericardium.

In some embodiments, the arcuate edges of the respective plurality of leaflets are sutured to the stent.

In certain embodiments, the stent defines a volume extending therethrough and each leaflet is disposed within the volume defined by the stent. For example, the arcuate edges of the respective plurality of leaflets can be coupled to an end portion of the stent.

In some embodiments, the leaflets are movable between an open position permitting flow past the stent in the expanded, unstressed state and a closed position substantially restricting flow past the stent in the expanded, unstressed state.

Embodiments can include one or more of the following advantages.

In some embodiments, the ratio of the surface area of the belly to the outer cross-sectional area of the expanded stent is about 0.09 to about 0.16. This range of ratios can facilitate sheathing the replacement valve with a sheathing force below about 30 lbs (e.g., below about 20 lbs, below about 10 lbs) just prior to intraluminal delivery to the body passageway of the patient while also allowing the replacement valve to regulate properly the flow of blood at the implantation site in the body passageway.

In certain embodiments, the arcuate edge that defines at least a portion of the belly of each leaflet is sutured to the expandable stent. This can allow the leaflet assembly to expand as the stent expands at the implantation site. Additionally or alternatively, suturing the arcuate edge of the leaflet to the expandable stent can reduce pressure gradients that could otherwise deteriorate the physical integrity of the leaflet over time.

In some embodiments, the arcuate edges of the respective leaflets are coupled to the stent in a plane (e.g., a plane defined by an end of the stent). This can facilitate reliable alignment of the leaflet assembly with respect to the expandable stent and, thus, reduce the likelihood that the leaflet assembly will come into contact with the expandable stent during normal opening and closing of the replacement valve.

In certain embodiments, the included angle between each side portion and the tangent to a respective end of the arcuate edge is greater than about 90 degrees. This can reduce the likelihood of delamination of the leaflet during preparation of the leaflet assembly and/or during use. In embodiments in which the leaflets are die cut from a flat sheet of biological material, angles greater than about 90 degrees additionally or alternatively reduce the likelihood that the die will warp over time to produce leaflets having variable sizes.

Other features, objects, and advantages will be apparent from the description and drawings, and from the claims.

DESCRIPTION OF DRAWINGS

FIGS. 6A-6D are schematic representations of the process of sheathing the replacement valve of FIG. 1.

Like reference symbols in the various drawings indicate like elements.

DETAILED DESCRIPTION

Figure 1:
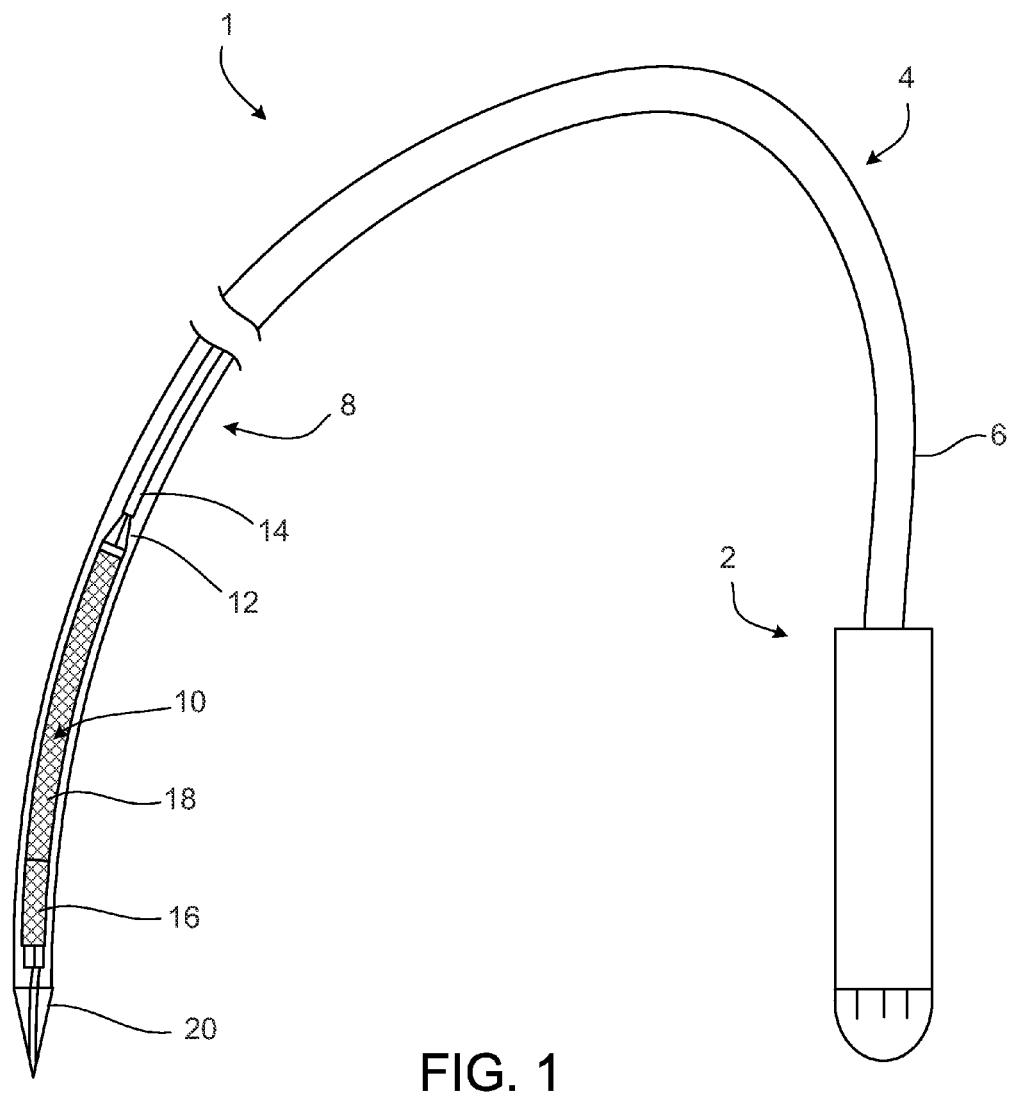
FIG. 1 is a partial cut-away view of a replacement valve in an unexpanded delivery configuration within a delivery system.
Figure 2:
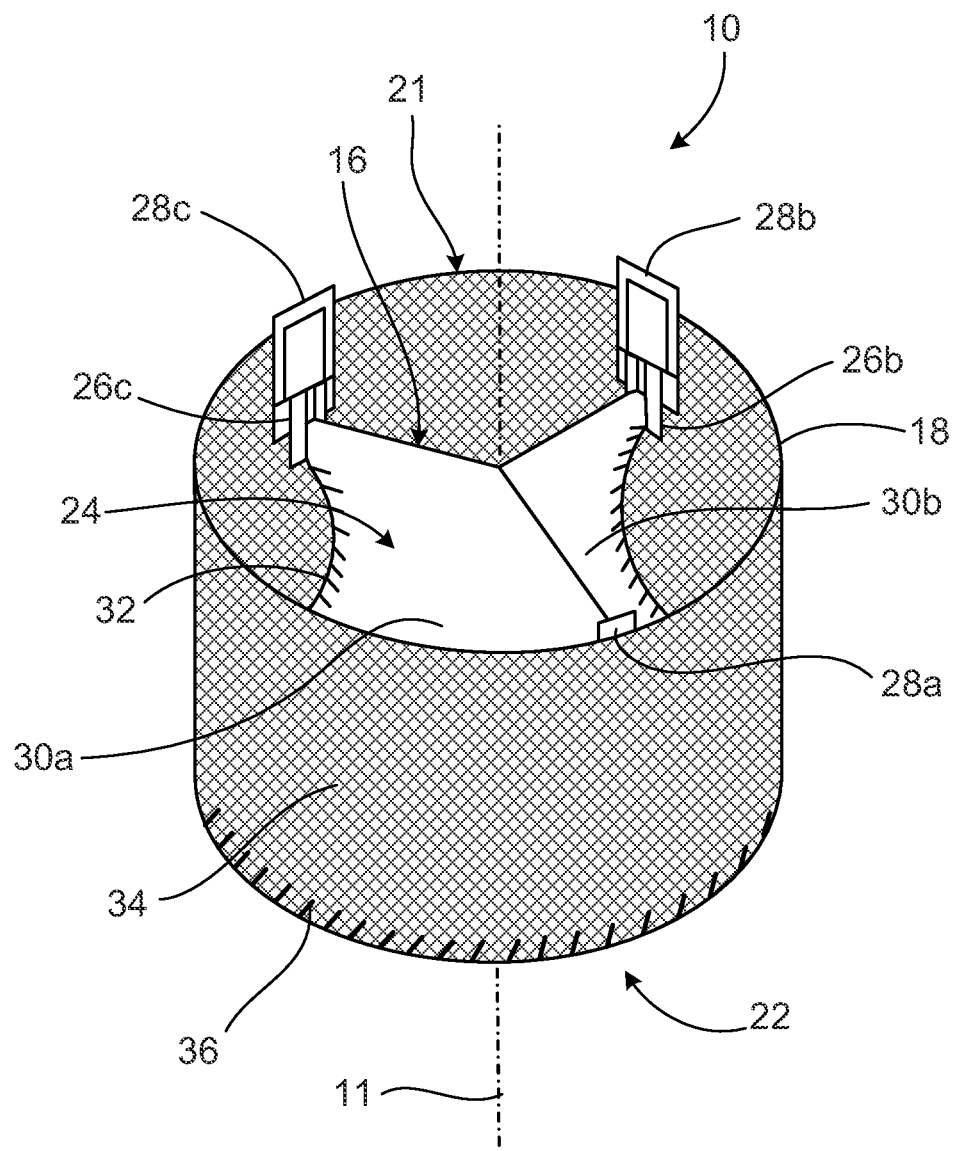
FIG. 2 is an isometric view of the replacement valve of FIG. 1 in an expanded state.
Figure 3:
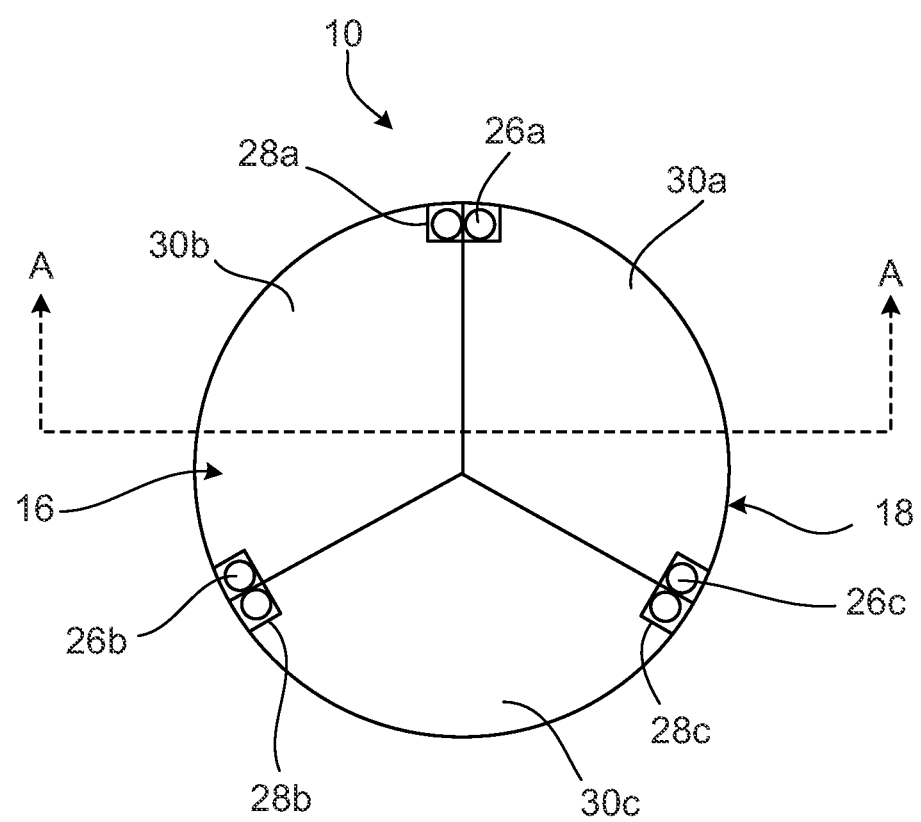
FIG. 3 is a top-down, plan view of the replacement valve of FIG. 1.
Figure 4:
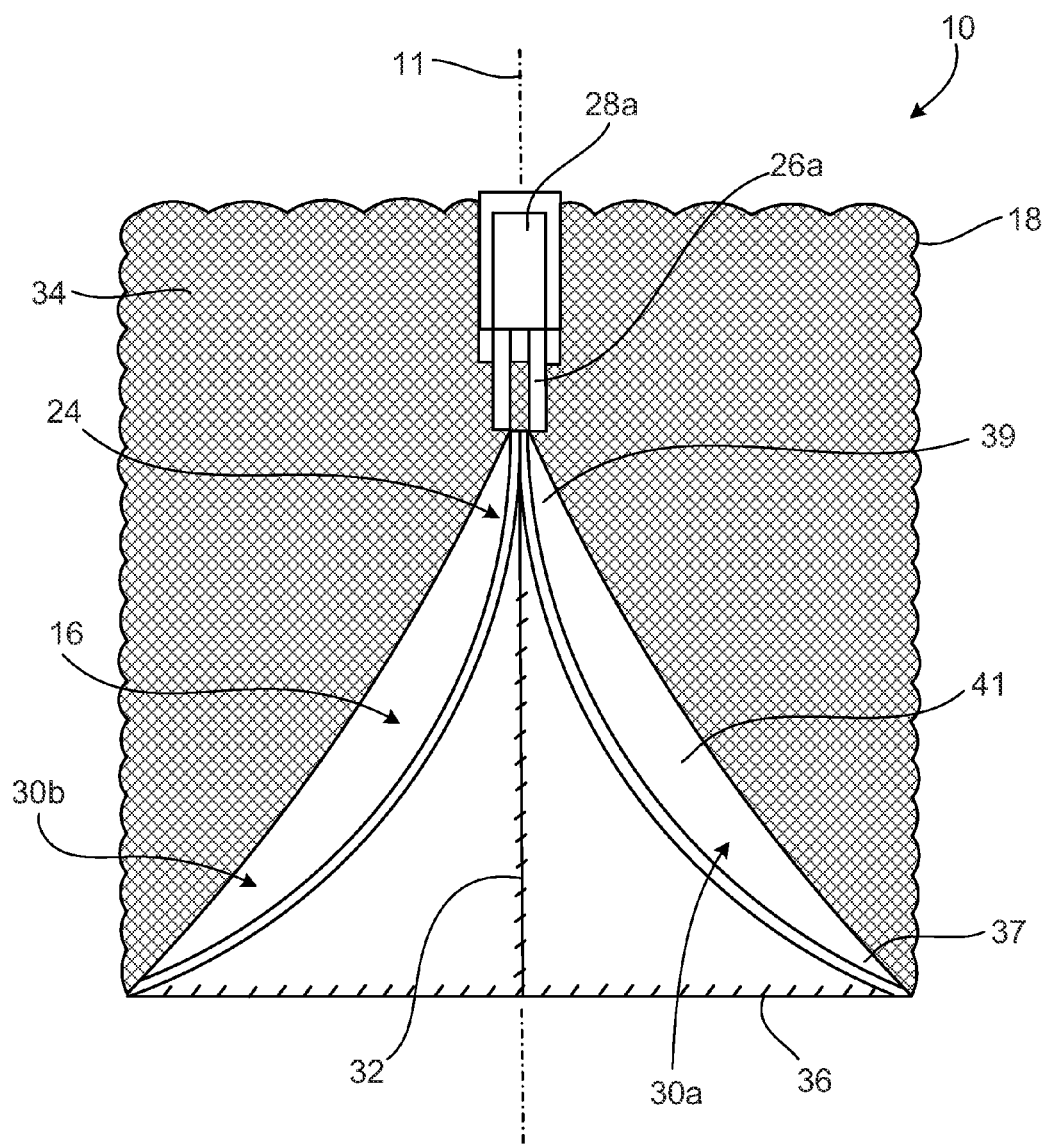
FIG. 4 is a cross-sectional view of the replacement valve of FIG. 1, taken along the line A-A of FIG. 3.
Figure 5:
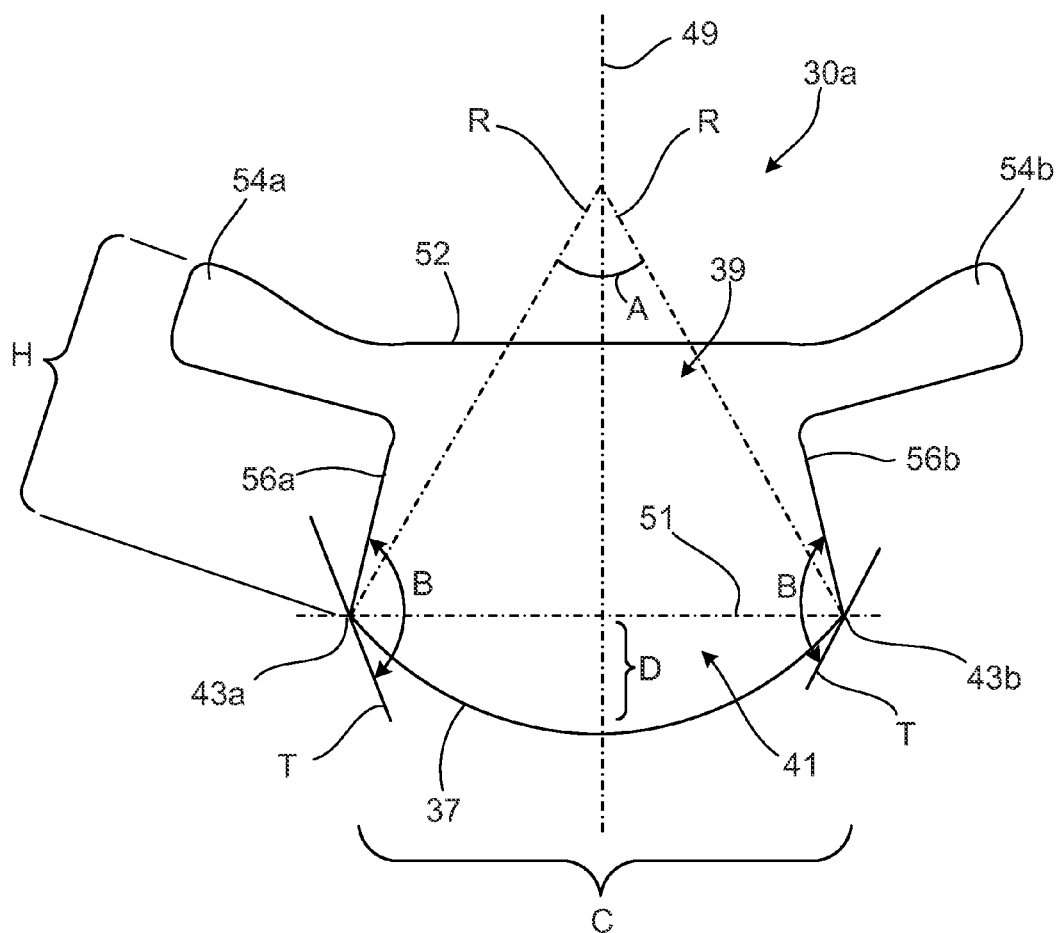
FIG. 5 is a top, plan view of a flattened leaflet of the replacement valve of FIG. 1.
Figure 7A:
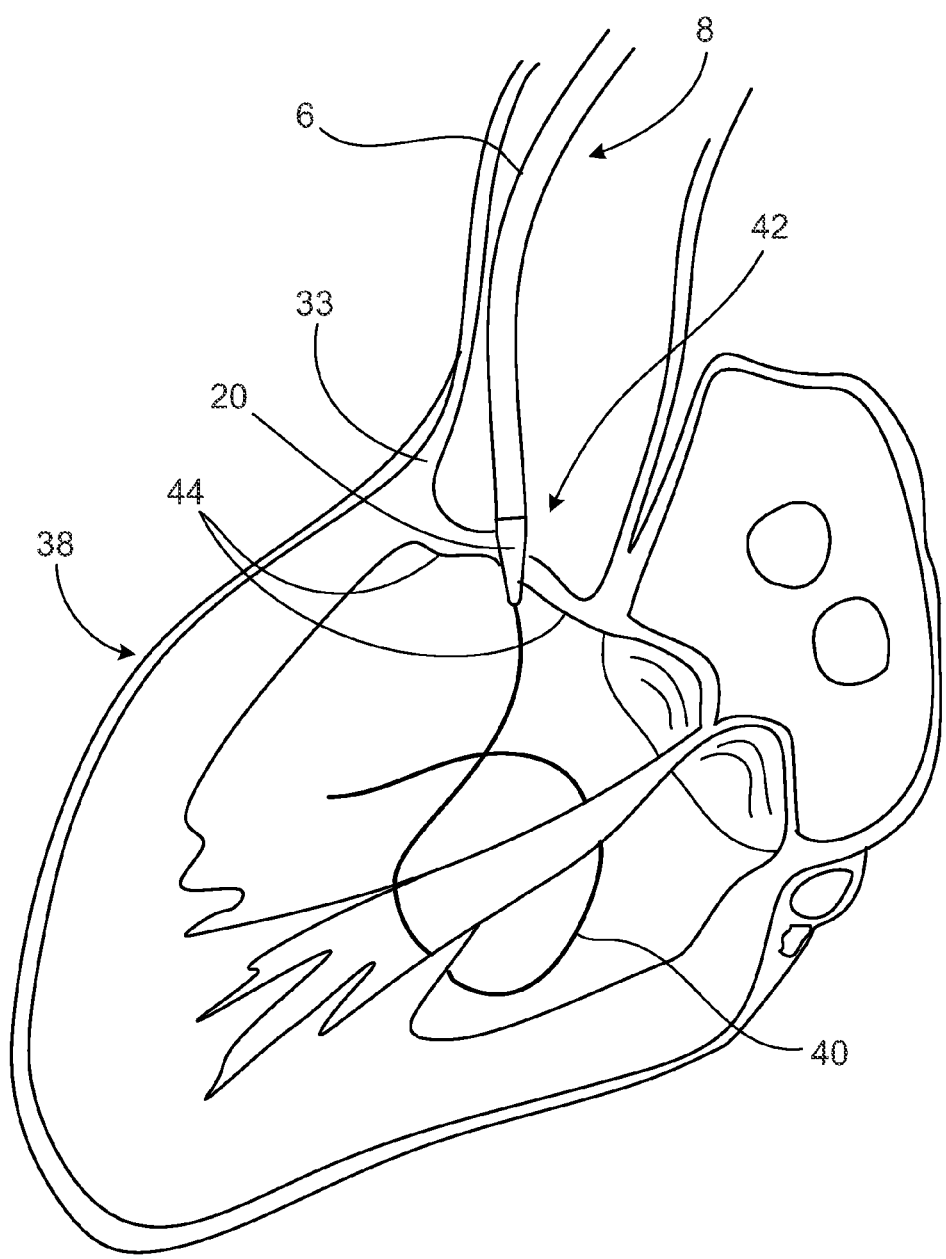
FIGS. 7A-7C are schematic representations of the deployment of the replacement valve of FIG. 1 to replace an aortic valve.
Figure 7B:
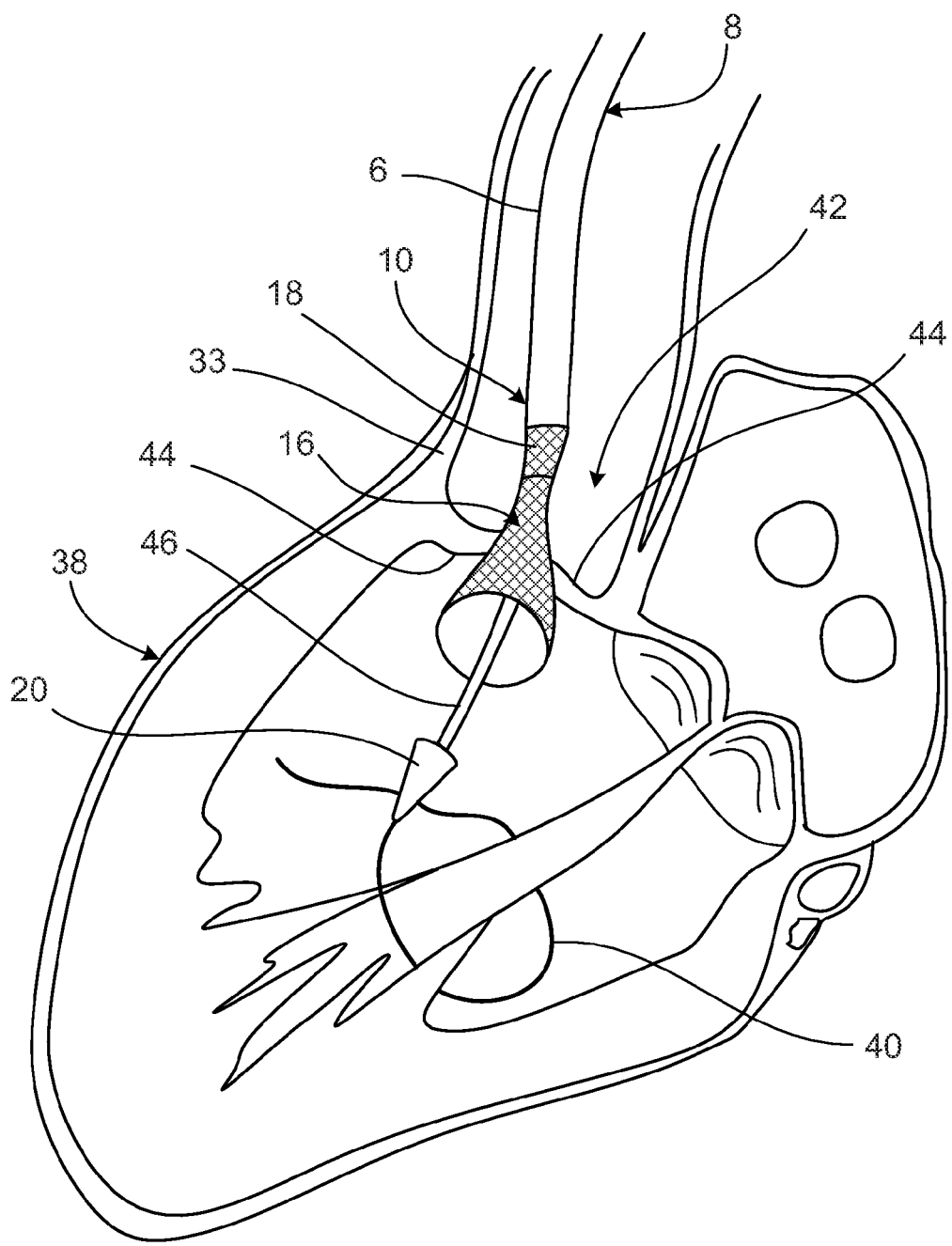
Figure 7C:
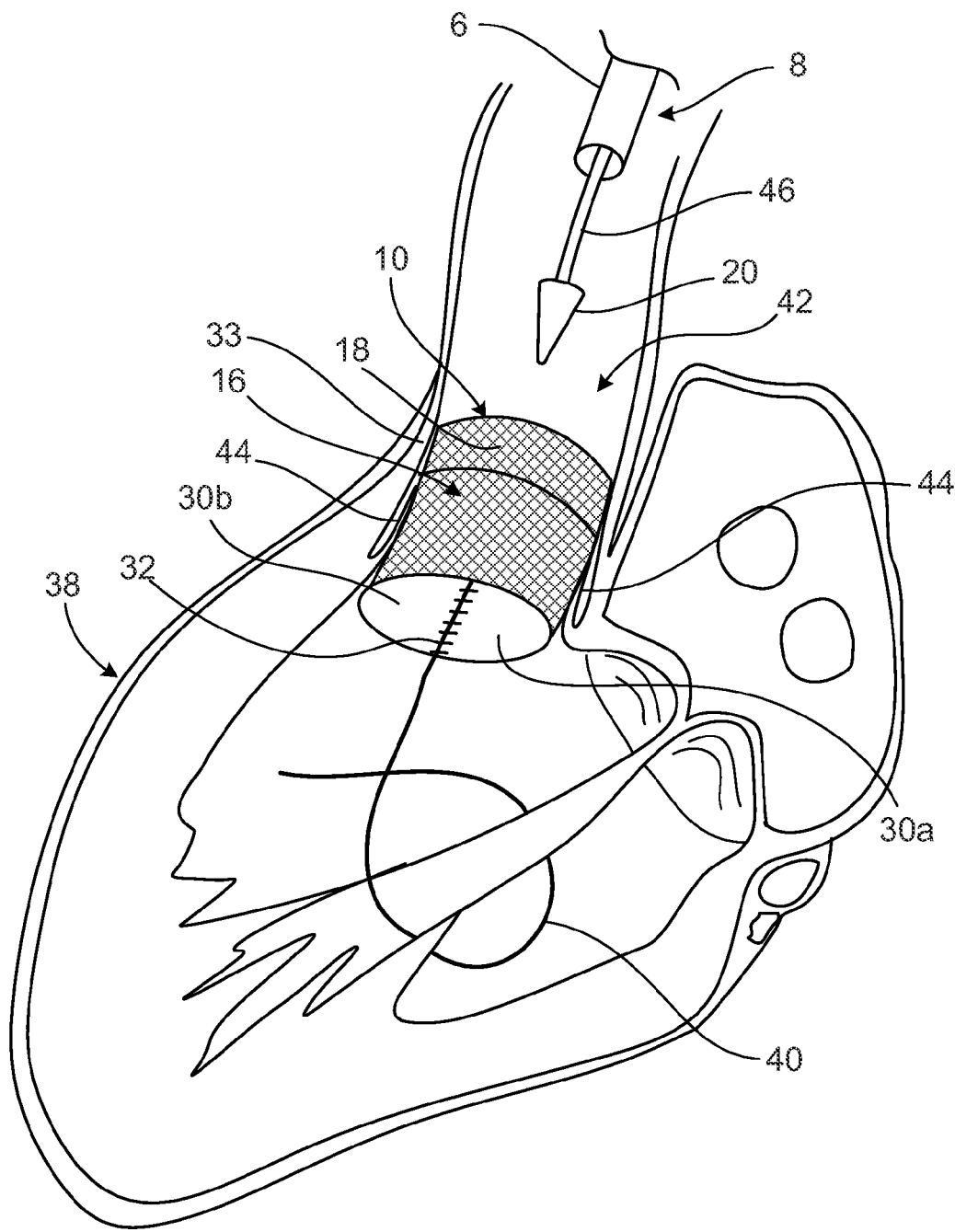

Referring to FIG. 1, a delivery system 1 includes a control handle 2, an external sheath 4, and a replacement valve 10. In the undeployed configuration shown in FIG. 1, a distal portion 8 of the external sheath 4 is disposed about the replacement valve 10 in an unexpanded state such that the replacement valve 10 can be moved through a body passageway (e.g., a femoral artery) to an implantation site (e.g., an aortic valve) with minimal invasiveness and/or trauma to the implant recipient. For example, a multi-lumen catheter 14 can be disposed within the external sheath 4 and, as described in further detail below, the replacement valve 10 can be advanced through a body passageway, to an implantation site, by moving the multi-lumen catheter 14 over a guidewire (not shown in FIG. 1) extending through the delivery system 1 from the control handle 2 to a nosecone 20 at the distal portion 8 of the external sheath 4.

As also described in further detail below, the control handle 2 can be manipulated to move the distal portion 8 of the external sheath 4 distally over the replacement valve 10 to compress the replacement valve 10 to the unexpanded state shown in FIG. 1. This process is often referred to as sheathing and can be done, for example, just prior to implantation. By reducing the amount of time the replacement valve 10 is in the unexpanded state, sheathing the replacement valve 10 just prior to implantation (e.g., less than about 8 hours before implantation) can reduce the amount of overall stress placed on the replacement valve 10 since the replacement valve 10 can be shipped and stored in an expanded, unstressed state. Additionally or alternatively, sheathing the replacement valve 10 just prior to implantation can allow the replacement valve 10 to be stored in a solution (e.g. a moistening solution) to preserve the mechanical integrity of the biological tissue that may be part of the replacement valve 10. As another example, sheathing the replacement valve 10 just prior to implantation can allow the replacement valve 10 to be inspected prior to implantation.

Once the replacement valve 10 has been sheathed and advanced through a body passageway to the implantation site, the control handle 2 is manipulated to move the distal portion 8 of the external sheath 4 proximally to expose the replacement valve 10 at the implantation site. As described in further detail below, the exposed replacement valve 10 can radially expand from the unexpanded state for intraluminal delivery through a body passageway to an expanded state for implantation of the replacement valve in the body passageway. In some embodiments, the replacement valve 10 can be partially deployed, resheathed (e.g., by advancing the external sheath 4 distally), and then redeployed. This can improve placement of the replacement valve 10 within the body passageway. In certain embodiments, the replacement valve 10 is mechanically expanded from the unexpanded state to at least a portion of the expanded state. For example, as shown in FIG. 1, actuation elements 12 can extend through the multi-lumen catheter 14 to engage the replacement valve 10. Continuing with this example, the replacement valve 10 self-expands upon withdrawal of the distal portion 8 of the external sheath 4 and the control handle 2 moves actuation elements 12 to further expand the replacement valve 10 (e.g, by foreshortening the valve) for engagement with the body passageway at the implantation site.

Referring now to FIGS. 1-5, the replacement valve 10 includes a leaflet assembly 16 and a stent 18. The leaflet assembly 16 is coupled to the stent 18 such that the leaflet assembly 16 is disposed within the volume defined by the stent 18. Thus, for example, the leaflet assembly 16 is disposed within the volume defined by the stent 18 when the stent 18 is in the unexpanded state and is being moved through the body passageway. The leaflet assembly 16 is also disposed within the volume defined by the stent 18 when the stent is in the expanded state at the implantation site.

The stent 18 is substantially tubular and defines a volume extending from a first end portion 21 to a second end portion 22 and defines an outer diameter of the replacement valve. The substantially tubular shape of the stent 18 can be defined by 1, 2, 3, or 4 braided wires (e.g., wires each having an outer diameter of about 0.008 inches to about 0.020 inches). In some embodiments, the stent 18 is nitinol. In certain embodiments, the stent 18 has a diameter of about 20 mm to about 30 mm in an expanded, unstressed state. When the stent 18 is in the expanded state in a body passageway, the expanded stent engages the body passageway to hold the replacement valve 10 in place.

The leaflet assembly 16 is substantially symmetrically disposed about a center axis 11 defined by the stent 18 in a fully expanded, unstressed state. This symmetry can be facilitated by aligning the leaflet assembly 16 with respect to a substantially planar opening defined by the second end portion 22 of the stent 18.

The leaflet assembly 16 includes three leaflets 30a, 30b, 30c and posts 26a, 26b, 26c. Each post 26a, 26b, 26c is coupled (e.g., sutured) to an interior surface of the stent 18, substantially evenly spaced about the interior surface of the stent 18. This relative positioning of the posts 26a, 26b, 26c can facilitate symmetric mounting of the leaflets 30a, 30b, 30c relative to the expanded, unstressed stent 18. Each post 26a, 26b, 26c is substantially cylindrical and coupled (e.g., sutured) to an interior surface of the stent 18 such that a longitudinal axis of each post 26a, 26b, 26c is substantially parallel to the center axis 11 of the expanded stent 18. Buckles 28a, 28b, 28c are coupled to the stent 18 along the interior surface of the stent 18 and are substantially aligned with respective posts 26a, 26b, 26c. Actuation elements 12 can draw the first and second end portions 21, 22 of the stent 18 toward one another to move the posts 26a, 26b, 26c toward buckles 28a, 28b, 28c. Additionally or alternatively, the actuation elements 12 can draw the first and second end portions 21, 22 of the stent 18 toward one another (e.g., to foreshorten the stent 18) to expand the stent 18 radially into secure engagement with the body passageway. In some embodiments, the stent 18 is radially expandable from a first size for intraluminal delivery to a second size and is further radially expandable by moving the first and second end portions 21, 22 of the stent 18 toward one another.

For the sake of clarity, the geometry and mounting of leaflet 30a is described below. It should be appreciated, however, that leaflets 30a, 30b, and 30c are substantially identical, varying only with respect to thickness and flexibility associated with biological tissue. Thus, the respective geometries and mounting of leaflets 30b and 30c are analogous to the geometry and mounting of leaflet 30a.

The leaflet 30a has an arcuate edge 37, a coaptation portion 39, and a belly 41, with the leaflet 30a having a substantially symmetrical geometry about a first axis 49 extending generally in a direction from the arcuate edge 37, through the belly 41, and to the coaptation portion 39. Side portions 56a and 56b are disposed on either side of the first axis 49 and each side portion 56a, 56b extends from a respective first and second end 43a, 43b of the arcuate edge 37 toward the coaptation portion 39. Similarly, tabs 54a and 54b are disposed toward the coaptation portion 39 on either side of the first axis 49, with a free edge 52 extending therebetween. The tabs 54a and 54b extend away from respective side portions 56a and 56b. The side portions 56a and 56b are non-parallel to one another (e.g., converging toward the first axis 49) such that a width of the arcuate edge 37 is greater than the width of the coaptation portion 39. This can reduce the likelihood that the coaptation portion 39 of the leaflet 30a will come into contact with the stent 18 as the coaptation portion 39 moves into and out of contact with the respective coaptation portions of the other leaflets as the replacement valve 10 moves between the open and closed position.

Tabs 54a and 54b are coupled (e.g., sutured) to posts 26a and 26c, respectively, which are disposed toward a first end portion 21 of the stent 18. As described in further detail below, the arcuate edge 37 is coupled to the second end portion 22 of the stent 18. With leaflet 30a mounted to the stent 18 at tabs 54a,b and to the arcuate edge 37, the free edge 52 of the leaflet 30a can move into and out of coaptation with the respective free edges of the leaflets 30b,c, which are mounted in an analogous manner. Accordingly, the mounted leaflets 30a, 30b, 30c are movable between an open position (permitting flow past the expanded stent 18) when fluid flows from a second end portion 22 to a first end portion 21 of the expanded stent 18 and a closed position (substantially restricting flow past the expanded stent 18) when fluid flows from the first end portion 21 to the second end portion 22 of the expanded stent 18. In the closed position (shown in FIGS. 3 and 4), the leaflets 30a, 30b, 30c are coaptable with one another to define a coaptation region 24. At least a portion of the coaptation region 24 is disposed substantially along the center axis 11 of the stent 18 when the stent 18 is in an expanded, unstressed state.

As described in further detail below, as the replacement valve 10 is sheathed into the compressed state (shown in FIG. 1), at least a portion of the leaflet assembly 16 folds upon itself. Thus, in general, the sheathing forces required to compress the replacement valve 10 can increase as the overall volume of material used in the leaflet assembly 16 increases. For a given leaflet thickness, the surface area of the belly 41 relative to the cross-sectional area of the stent 18 is selected to achieve sheathing forces within an acceptable range (e.g., such that the replacement valve 10 can be reliably sheathed by an operator just before implantation). The physical requirements of the replacement valve 10 can impose limits on the minimal surface area of the belly 41 required to achieve acceptable sheathing forces while also resulting in proper functioning of the leaflet assembly 16. As used herein, the surface area of the belly 41 is used to refer to the surface area of the belly 41 on a single side of the leaflet 30a and approximates the belly 41 as ideally planar (e.g., does not account for natural variations in the thickness of the biological tissue that forms the belly 41).

The leaflet 30a has a height H which is the distance from the first end 43a to the free edge 52, along an axis defined by the side edge 56a. In some embodiments, the height of the leaflet is about 10 mm to about 20 mm (e.g., about 12 mm to about 16 mm; about 14 mm). In some embodiments, the leaflet height H fits within a volume defined by the stent 18. In certain embodiments, the leaflet height H is such that the overall leaflet assembly 16 can move between an open position that allows a sufficient amount of fluid to flow therethrough and a closed position that substantially prevents the flow of fluid therethrough (e.g., reducing the likelihood of regurgitation as blood flow reverses through an implanted replacement valve 10 acting to replace the aortic valve of the implant recipient). For example, the leaflet height H can be fixed such that the overall leaflet assembly 16 has a large coaptation region 24 (e.g., about 3 mm to about 6 mm) that can reduce the likelihood of regurgitation if the replacement valve 10 is implanted at an implantation site that is non-circular (e.g., on a deposit and/or on fused native leaflets).

The arcuate edge 37 of the leaflet 30a extends along an arc from the first end 43a to the second end 43b. The first end 43a and the second end 43b of the arcuate edge 37 define an axis 51 such that the distance from the first end 43a to the second end 43b along the axis 51 is a chord length C. The axis 51 lies substantially between the arcuate edge 37 and the coaptation portion 39, and the belly 41 extends from the arcuate edge 37 to the axis 51 defined by the first and second ends 43a,b.

As one physical requirement on the size of the belly 41, the total arc length of the arcuate edge 37 is substantially equal to about one-third of the inner circumference of the stent 18 in the expanded, unstressed state such that the total arc length of the leaflets 30a, 30b, 30c is substantially equal to the inner circumference of the stent 18 in the expanded, unstressed state. For example, the arc length of each of the leaflets 30a, 30b, 30c can be about one-third (e.g., slightly more than one-third to accommodate stitching) of the inner circumference of the stent in the expanded, unstressed state. Given that the leaflets 30b and 30c have geometries similar to that of leaflet 30a, this sizing of the respective arcuate edges 37 of each leaflet 30a,b,c can allow the leaflets 30a,b,c to be coupled to the stent 18 (e.g., by stent sutures 36) to cover the inner circumference of the expanded stent 18 in the expanded, unstressed state. For example, the respective arcuate edges 37 of leaflets 30a,b,c can be attached to the second end portion 22 of the stent 18 by stent sutures 36. In some embodiments, the arcuate edges 37 of the leaflets 30a,b,c are secured to the stent 18 to lie substantially along a plane. In certain embodiments, the second end portion 22 of the stent 18 lies in a plane (e.g., when the stent 18 is in the expanded, unstressed state) and the respective arcuate edges 37 of the leaflets 30a,b,c are disposed along the plane defined by the second end portion 22. Attachment of the arcuate edges 37 of the leaflets 30a,b,c in a plane defined by the second end portion 22 of the stent 18 can, for example, facilitate alignment of the leaflet assembly 16 relative to the stent 18 and, in turn, reduce the likelihood of uneven wear of the leaflets 30a,b,c that could result from misalignment.

As another physical requirement of the belly 41, the chord length C must be a length sufficient to allow the respective side edges 56a,b of the leaflets 30a,b,c to come into contact with one another to be sutured together (e.g., at leaflet sutures 32). The leaflet 30a is sutured to each of the other leaflets by leaflet sutures 32 extending generally in a direction from the arcuate edge 37 to the coaptation portion 39 of each leaflet. The coaptation portion 39 of leaflet 30a is coupled to two posts 26a, 26c such that the coaptation portion 39 of leaflet 30a is movable relative to the respective coaptation portions 39 of each of the other leaflets as the leaflets 30a, 30b, 30c move from the closed position to the open position. In some embodiments, leaflet 30a is sized relative to the expanded dimension of the stent 18 such that the belly portion 41 of the leaflet 30a is spaced from the stent 18 as the leaflet 30a moves in response to changes in flow through the replacement valve 10. This relative spacing can, for example, reduce the likelihood that the leaflet 30a will wear out through repeated contact with the stent.

The chord length C must also be a length sufficient to allow the side edges 56a,b of a single leaflet (e.g., leaflet 30a) to be spaced apart by a distance sufficient to allow the pressure drop through the replacement valve 10 (in the open position) to be less than about 20 mmHg (e.g., less than about 15 mmHg) for all flow conditions and/or to fall within the range of pressure drops associated with a normally functioning, native aortic valve.

Given that the total arc length of the arcuate edge 37 and the chord length C are fixed physical requirements, the size of the belly 41 can be adjusted by adjusting a height D of the belly 41, where the height D of the belly 41 is the maximum distance between the arcuate edge 37 and the axis 51 defined by the first end 43a and the second end 43b of the arcuate edge 37. In general, the height D of the belly 41 can be reduced by increasing the radius of curvature R of the arcuate edge 37 and, thus, also reducing the included angle A swept along the radius of curvature to define the arcuate edge 37. For example, if the arc length of the arcuate edge 37 is fixed at 27 mm, the height D of the leaflet 30a can be reduced from about 4 mm to about 2 mm by increasing the radius of curvature from about 22 mm (within an included angle of about 70 degrees) to about 44 mm (with an included angle of about 35 degrees).

As an additional physical requirement of the belly 41, an included angle B between each side portion 56a,b and a tangent T to a respective end 43a,b is greater than about 90 degrees. The leaflet 30a can be cut from a flat sheet of a biological tissue (e.g., bovine pericardium, equine pericardium, and/or porcine pericardium) having a thickness of between about 0.010 inches to about 0.015 inches such that the leaflet 30a will have a thickness in this range. Requiring the included angle B to be greater than about 90 degrees can reduce the likelihood of physical deterioration (e.g., delamination) of the leaflet 30a over time. Additionally or alternatively, requiring the included angle B to be greater than about 90 degrees can facilitate uniform cutting of the leaflet 30a by avoiding the need to cut the leaflet 30a using a die having acute dimensions that can deteriorate over time (e.g., a 90 degree angle on the die becoming rounded after repeated use).

Given the physical requirements of the belly 41, the ratio of the surface area of the belly 41 to the outer cross-sectional area of the expanded stent 18 is about 0.05 to about 0.25 (e.g., about 0.09 to about 0.16). This range of ratios can facilitate sheathing the replacement valve 10 with acceptable sheathing forces (e.g., below about 40 lbs, below about 30 lbs, below about 20 lbs, below about 10 lbs), while also resulting in a replacement valve 10 with hemodynamic performance acceptable for replacement of a native aortic valve. In embodiments in which the outer diameter of the expanded stent 18 is in the range (e.g., about 20 mm to about 30 mm; about 23 mm to about 27 mm) suitable for aortic valve replacement in humans, the maximum distance between the arcuate edge 37 and the axis 51 defined by the first and second ends 43a,b is about 1 mm to about 6 mm (e.g., about 2 mm to about 4 mm). Additionally or alternatively, in these embodiments, the radius R of the arcuate edge 37 is about 10 mm to about 50 mm (e.g., about 20 mm to about 50 mm) and the included angle is about 25 degrees to about 90 degrees (e.g., about 35 degrees to about 70 degrees).

For the sake of clarity, the belly 41 of the leaflet 30a was discussed above. It will be appreciated that analogous design considerations apply to the leaflets 30b, 30c such that each leaflet of the leaflet assembly 16 includes a belly 41 with the physical characteristics described above.

Referring now to FIGS. 1 and 6A-D, the replacement valve 10 is shipped in the open position (FIG. 6A) such that, for example, the leaflet assembly 16 can be stored in a moistening solution (e.g., saline) to preserve the tissue of the leaflets 30a, 30b, 30c. Just prior to implantation, the replacement valve 10 is sheathed by advancing the distal portion 8 of the external sheath 4 toward the nosecone 20. As the distal portion 8 of the external sheath 4 passes over the actuation elements 12, the sheathing force is about 2 lbs. Similarly, as the distal portion 8 of the external sheath 4 moves over the buckles 28a,b,c, the sheathing force remains about 2 lbs. As the distal portion 8 of the external sheath 4 is moved further distally and passes over the leaflet assembly 16, the sheathing forces increase to about 10 lbs. Finally, as the distal portion 8 of the external sheath 4 is moved even further distally and passes over the portion of the leaflet assembly 16 corresponding to the belly 41 (shown in FIG. 5) of each leaflet 30a,b,c, the sheathing force can increase significantly. This significant increase can be attributed to the leaflets 30a,b,c doubling on themselves and as well as the suturing material (e.g., stent sutures 36 and leaflet sutures 32, shown in FIG. 2) present in that portion of the replacement valve 10. As compared to replacement valves having higher ratios of belly area to outer cross-sectional area of the stent, the use of leaflets 30a,b,c having such a ratio between about 0.09 to about 0.16 have reduced spikes in sheathing force during the last portion of the sheathing process. Moreover, the leaflets 30a,b,c having a ratio in this range can function properly given the other physical constraints of the replacement valve 10 for proper anatomical performance.

Referring now to FIGS. 1 and 7A-C, the delivery system 1 can be used for intraluminal delivery of the replacement valve 10 to an aortic valve 42 of a mammalian heart 38, where the replacement valve 10 can be deployed without the need for excising the native leaflets 44 of the aortic valve 42. The distal portion 8 of the delivery system 1 is moved over a guidewire 40 (e.g., by manipulation of the control handle 2) until the nosecone 20 moves past the native leaflets 44. With the distal portion 8 of the delivery system 1 in place, the external sheath 6 is retracted (e.g., by manipulation of the control handle 2) to release the replacement valve 10. The released replacement valve 10 can expand radially under the self-expanding force of the stent 18. Additionally or alternatively, the released replacement valve 10 can expand radially under the force of the actuation elements 12, which can also be manipulated by the control handle 2.

The force of the fully expanded stent 18 secures the replacement valve 10 to the wall of the aortic valve 42 and pins the native leaflets 44 to an aortic wall 33. With the native leaflets 44 pinned in this position, the leaflet assembly 16 opens and closes in response to the pulsatile flow of blood through the heart 38 and, in this way, acts to replace the aortic valve 42. After the replacement valve 10 has been fully deployed in the aortic valve 42, the nosecone 20 can be retracted proximally through the valve by an inner tube 46 and the distal portion 8 of the delivery system 1 can be retracted proximally along the guidewire 40 until the delivery system 1 is removed from the recipient of the replacement valve 10.

A number of embodiments of the invention have been described. Nevertheless, it will be understood that various modifications may be made without departing from the spirit and scope of the invention. For example, a replacement valve can include a fabric ring disposed toward the distal end of the valve such at least a portion of the stent sutures that secure the respective arcuate edges of the leaflets to the stent additionally or alternatively pass through the fabric ring. Accordingly, other embodiments are within the scope of the following claims.

What is claimed is:

1. A prosthetic heart valve comprising:
   a stent having an outer cross-sectional area, the stent radially expandable to an expanded, unstressed state; and
   a plurality of leaflets, each leaflet comprising
      a coaptation portion movable relative to respective coaptation portions of the other leaflets,
      an arcuate edge having a first end and a second end, the arcuate edge coupled to the stent, and
      a belly extending from the arcuate edge to an axis defined by the first and second ends of the arcuate edge, wherein the ratio of the surface area of the belly to the outer cross-sectional area of the stent in the expanded, unstressed state is about 0.09 to about 0.16.

2. The prosthetic heart valve of claim 1 wherein the stent in the expanded, unstressed state has an outer diameter of about 20 mm to about 30 mm.

3. The prosthetic heart valve of claim 1 wherein the arcuate edge has a radius of about 20 mm to about 50 mm and an included angle of about 35 degrees to about 70 degrees.

4. The prosthetic heart valve of claim 1 wherein a maximum distance between the arcuate edge and the axis defined by the first and second ends of the arcuate edge is about 2 mm to about 4 mm.

5. The prosthetic heart valve of claim 1 wherein the arcuate edges of the respective leaflets are coupled to the stent in a plane.

6. The prosthetic heart valve of claim 5 wherein the plane is defined by an end of the stent.

7. The prosthetic heart valve of claim 1 wherein the total arc lengths of the arcuate edges of the plurality of leaflets, as coupled to the stent, is about equal to an inner circumference of the expanded stent.

8. The prosthetic heart valve of claim 1 wherein each leaflet is substantially symmetrical about an axis of the leaflet extending in a direction from the coaptation portion to the arcuate edge.

9. The prosthetic heart valve of claim 1 wherein the arcuate edge is opposite the coaptation portion.

10. The prosthetic heart valve of claim 9 wherein each of the plurality of leaflets further comprises first and second side portions extending from respective first and second ends of the arcuate edge toward the coaptation portion.

11. The prosthetic heart valve of claim 10 wherein the first and second side portions of each leaflet are nonparallel to each other.

12. The prosthetic heart valve of claim 11 wherein, for each leaflet, the maximum width of the coaptation portion is less than the maximum width of the arcuate edge.

13. The prosthetic heart valve of claim 10 wherein at least one side portion of each leaflet is sutured to at least one side portion of each of the other leaflets.

14. The prosthetic heart valve of claim 10 wherein the included angle between each side portion and a tangent to a respective end of the arcuate edge is greater than about 90 degrees.

15. The prosthetic heart valve of claim 1 wherein each of the plurality of leaflets is biological tissue.

16. The prosthetic heart valve of claim 15 wherein the biological material is one or more of the following: bovine pericardium, equine pericardium, and porcine pericardium.

17. The prosthetic heart valve of claim 1 wherein the arcuate edges of the respective plurality of leaflets are sutured to the stent.

18. The prosthetic heart valve of claim 1 wherein the stent defines a volume extending therethrough and each leaflet is disposed within the volume defined by the stent.

19. The prosthetic heart valve of claim 18 wherein the arcuate edges of the respective plurality of leaflets are coupled to an end portion of the stent.

20. The prosthetic heart valve of claim 1 wherein the leaflets are movable between an open position permitting flow past the stent in the expanded, unstressed state and a closed position substantially restricting flow past the stent in the expanded, unstressed state.

* * * * *